United States Patent [19]
Itonaga et al.

[11] Patent Number: 5,807,266
[45] Date of Patent: Sep. 15, 1998

[54] FINGER-TYPE BLOOD PRESSURE METER WITH A FLEXIBLE FOLDABLE FINGER CUFF

[75] Inventors: Kazunobu Itonaga; Tameo Ashida, both of Osaka; Toshiyuki Kobayashi, Kyoto; Yoshihiko Sano, Kyoto; Takashi Inagaki, Kyoto, all of Japan

[73] Assignee: Omron Corporation, Kyoto-fu, Japan

[21] Appl. No.: 656,040

[22] Filed: May 24, 1996

[51] Int. Cl.⁶ ........................................................ A61B 5/00
[52] U.S. Cl. .......................... 600/499; 600/500; 600/479
[58] Field of Search .................................... 128/667, 672, 128/677, 680–3, 687–900, 686; 600/479, 485, 490, 493–6, 500–503, 499

[56] References Cited

U.S. PATENT DOCUMENTS 5,218,966  6/1993  Yamasawa ............................... 128/677

FOREIGN PATENT DOCUMENTS

A-06 125882  5/1994  Japan .
WO-A-81 03606  12/1981  WIPO .

Primary Examiner—Robert L. Nasser
Attorney, Agent, or Firm—Morrison & Foerster LLP

[57] ABSTRACT

A finger-type blood pressure monitor which is smaller for portability (when not in use). The monitor has a foldable finger cuff which can be stored in a compact case when it is not in use.

24 Claims, 13 Drawing Sheets

PRIOR ART

PRIOR ART

FINGER-TYPE BLOOD PRESSURE METER WITH A FLEXIBLE FOLDABLE FINGER CUFF

FIELD OF THE INVENTION

This invention concerns a finger-type blood pressure monitor which measures blood pressure off a patient's finger using a flexible folded finger cuff.

BACKGROUND OF THE INVENTION

As can be seen in FIG. 13, finger-type blood pressure monitors of the prior art include a main unit 70, a cuff housing 71 which extends at an angle past the main unit, and a finger cuff 72, which is housed in housing 71. With this type of monitor, the index finger of the left hand, for example, is inserted in the cuff 72 in housing 71. The button in operating unit 73 is then slid forward, causing cuff 72 to wrap tightly around the finger. Buttons 74 are used to turn the operating unit on and off and to start the blood pressure reading.

In another type of the conventional blood pressure monitor shown in FIG. 14, finger cuff housing 81 is supported so that it can rotate on main unit 80. A cover (not pictured) which encloses cuff housing 81 is mounted on main unit 80 so that it can easily be attached or removed. When the device is not being used, cuff housing 81 is pushed back into main unit 80. To use the device, one pushes button 83, which causes cuff housing 81 to pop out so that the patient can insert a finger in cuff 82. Finger cuff 82 includes an outer cuff, which will be inflated with air, and an inner cuff which is contained within the outer cuff. The inner cuff contains sensors which detect the pulse.

The conventional blood pressure monitor pictured in FIG. 13 experiences certain disadvantages. The fact that cuff housing 71 protrudes from main unit 70 increases the size of the monitor, making it cumbersome for use as a portable blood pressure monitor. When a user measures his or her blood pressure, the user must push buttons 74 with one hand while the index finger of the other is inserted in the cuff. The monitor thus requires the use of both hands. If a cylindrical cuff 72 is used, the cuff will already be cylindrical when one wishes to make a measurement. If the cuff remains cylindrical when the device is not in use, however, cuff 72 will have to be of an adequate thickness to allow this, making the device cumbersome for use as a portable monitor. Finally, it is possible for one or both of the operating buttons 74 to be actuated accidentally while the device is being transported, causing the cuff to be pressurized. This will cause unwanted exhaustion of the batteries.

The blood pressure monitor pictured in FIG. 14 experiences other disadvantages. With this monitor, the cover must be removed and cuff housing 81 must pop out, making it complicated to operate. To begin a measurement, one must first remove the cover, push button 83 to make cuff housing 81 pop out, and then push operating button (i.e., power supply switch) 84. This makes the monitor difficult to operate. If transparent windows are furnished in the portions of the outer cuff which correspond to the sensors to detect the pulse, the elasticity of those portions will be affected. This will lessen the ability of cuff 82 to pressurize the finger, resulting in lower measurement accuracy.

In addition, both the blood pressure monitor pictured in FIG. 13 and that pictured in FIG. 14 have the following disadvantages. In order to begin a measurement, the user must depress the switch to pressurize the cuff, which makes the operation of the device cumbersome. If the monitor has a memory, an additional switch will be required to access the memory.

SUMMARY OF THE INVENTION

This invention provides a finger-type blood pressure monitor with reduced size when it assumes its portable form (i.e., when it is not in use). The monitor of this invention is easier to operate than the prior art units described above. The monitor can be operated using only one hand. The finger cuff would be prevented from inflating when the monitor is being transported. The monitor can be produced at a lower cost than prior art monitors, while the accuracy of the measurements would be improved over that of prior art blood pressure monitors.

The blood pressure monitor of this invention includes a main unit; a cover for this main unit which is attached in such a way that it can open and close; a flexible foldable finger cuff of which a portion is fixed to the inside of the cover; and a chamber to contain the flexible foldable finger cuff in the main unit. When the cover is closed, the flexible foldable finger cuff is returned to its chamber. This type of blood pressure monitor thus becomes more compact when it is closed, making it less bulky to transport.

The blood pressure monitor of this application may also be designed so that when the cover is opened, the finger cuff orients itself so that the user can insert a finger into it. There is thus no need for the user to extract the cuff himself, so the monitor is easier to operate. When the cover is opened, the power supply may be automatically connected. There is no need to depress a power supply button, resulting in a monitor which is easier to operate. A timer or the like may be provided to cause pressurization of the cuff to begin after the cover has been opened. If the user inserts a finger into the cuff before it is pressurized, he will not need to actuate a button in order to pressurize it. The monitor is thus easier to operate than its predecessors. With the blood pressure monitor of this invention, the pulse may be detected and pressurization of the cuff begun as soon as the user inserts the finger in the cuff. The user does not need to push a button to start the measurement, so the monitor is easier to operate.

The blood pressure monitor disclosed in this application may be designed so that the start button is located on the portion of either the cover or the main unit which can be reached by the thumb when the index finger is inserted in the finger cuff. The button can then be actuated by the thumb while the finger is in the cuff, making it possible to operate the blood pressure monitor using only one hand.

The blood pressure monitor of this application may also be designed so that the cuff will not be pressurized when the actuating switch is depressed unless the detector has detected that the cover is open. Thus the cuff will not be pressurized if the switch is tripped accidentally while the monitor is being transported, thus preventing accidental operation.

The blood pressure monitor of this application can further be designed so that the actuating switch doubles as the memory access switch when the detector has not detected that the cover is open. In other words, a single switch serves as both the pressure actuating switch and the memory access switch. This reduces the number of operating switches required and lowers the cost of the product.

Finally, the blood pressure monitor of this application may be designed so that it has a main unit in which is provided a finger cuff with a number of sensors to detect the pulse. This blood pressure monitor is distinguished by the fact that the sensors are photoelectric sensors and by the fact that the infrared transmission factor of the portions of the cuff facing the pulse sensors is higher than that of the other portions of the cuff. With this design, the elasticity of the portions of the cuff will not be diminished nor will the ability to pressurize the cuff suffer. The result is an improvement in measurement accuracy.

BRIEF DESCRIPTION OF THE DRAWINGS

FIG. 1 shows the external appearance of a finger-type blood pressure monitor which is a preferred embodiment of this invention.

FIG. 2 shows another finger-type blood pressure monitor which is a second preferred embodiment of this invention.

FIG. 3 shows yet another finger-type blood pressure monitor of this invention.

FIG. 6 shows a finger cuff with a collar around its outer periphery.

DETAILED DESCRIPTION OF THE INVENTION

Figure 1A:
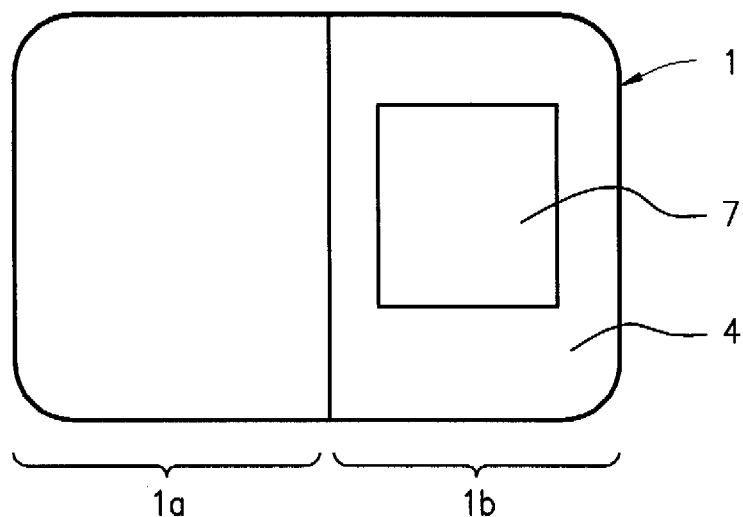
FIG. 1(a) is an overhead view.
Figure 1B:
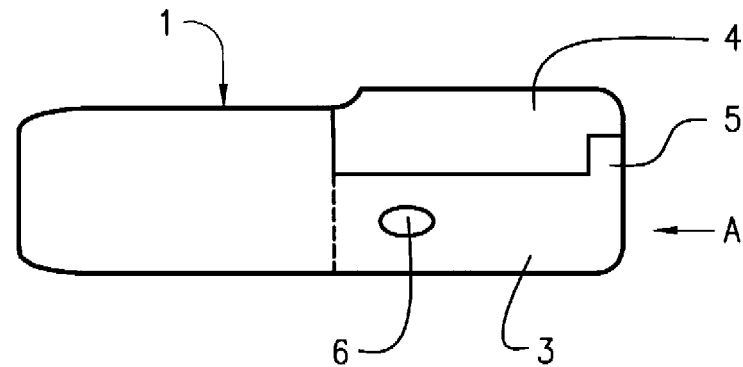
FIG. 1(b) is a lateral view.
Figure 1C:
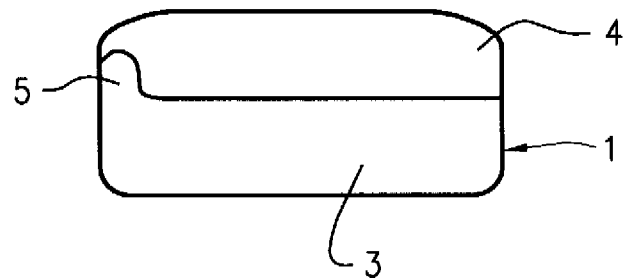
FIG. 1(c) is a lateral view from the direction indicated by arrow A in FIG. 1(b).

The external appearance of a blood pressure monitor which is a preferred embodiment of this invention is shown in FIG. 1. This finger-type blood pressure monitor comprises main unit 1; cover 4, which is attached to main unit 1 by hinge 5 in such a way that it can open and close; flexible foldable finger cuff 2 (not pictured in FIG. 1), a portion of which is fixed to the interior of cover 4; and chamber 3, in which the flexible foldable finger cuff is stored in main unit 1. On the exterior of cover 4 are display 7, which displays the blood pressure value; and operating button 6, which might, for example, be the switch to pressurize the cuff. Main unit 1 of this monitor is divided into two segments, 1a and 1b, of virtually the same size. Segment 1a contains the mechanism to pressurize the finger cuff (a pressure pump, a battery, a circuit board, a valve, etc.); segment 1b includes storage chamber 3 and cover 4, to which is attached display 7.

Figure 2A:
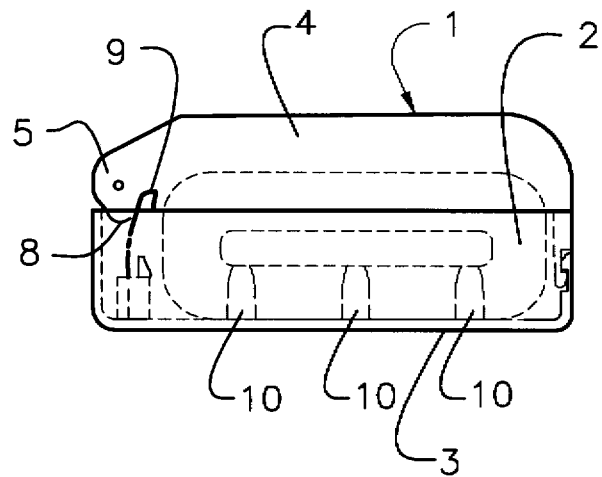
FIG. 2(a) is a lateral view of this monitor when closed.
Figure 2B:
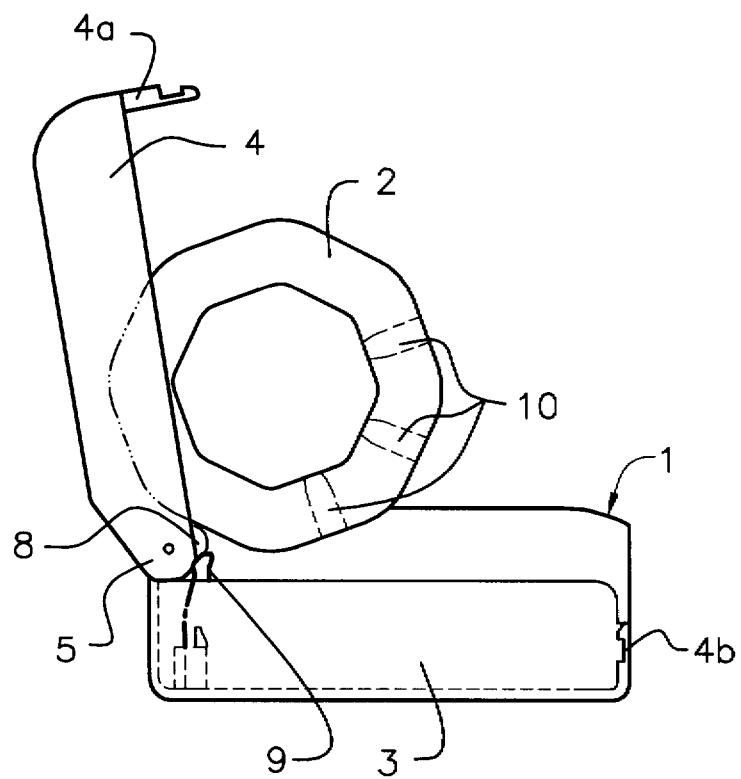
FIG. 2(b) is a lateral view of the same monitor when open.

FIG. 2 shows a finger-type blood pressure monitor which is somewhat different in appearance from that shown in FIG. 1. This monitor has a protruding catch 4a on the end of cover 4 and a corresponding indentation 4b on the interior surface of chamber 3. When cover 4 is closed, catch 4a engages with indentation 4b to insure that the cover will be securely closed. A portion of finger cuff 2 is fixed to the interior of cover 4. When cover 4 is opened, cuff 2 is drawn out of chamber 3 and assumes a cylindrical form suitable for the insertion of a finger. When cover 4 is closed, it pushes cuff 2 down so that it folds in two as it returns to chamber 3. Cuff 2 has three photoelectric sensors 10 to detect the pulse. The light from a luminous element within the cuff is emitted onto the finger, and the light reflected by the finger is detected by photodetector elements.

Figure 3A:
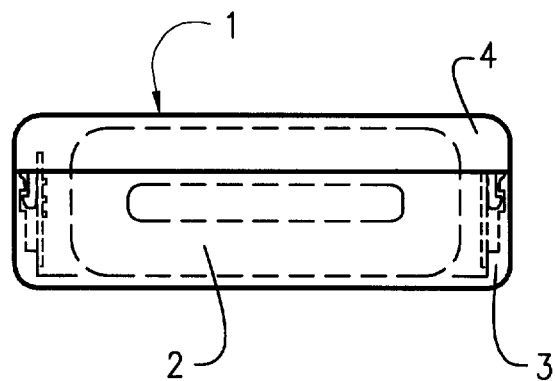
FIG. 3(a) is a lateral view of this monitor when closed.
Figure 3B:
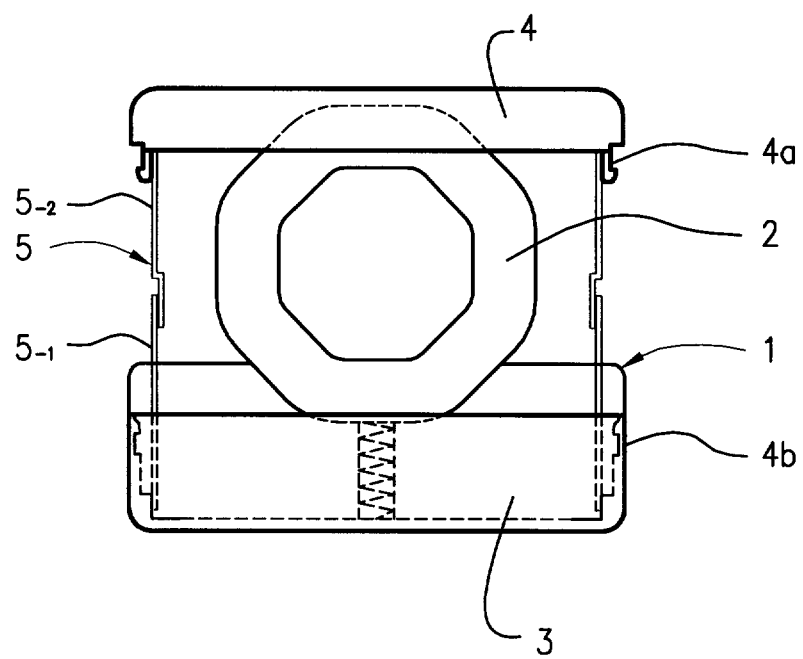
FIG. 3(b) is a lateral view of the same monitor when open.

FIG. 3 shows a different embodiment of a finger-type blood pressure monitor. In this embodiment, cover 4 pops up vertically. Hinges 5, which attach cover 4 to main unit 1 in such a way that it can be opened and closed, comprise segments 5-1, of which one end is supported within chamber 3 so that it is free to swing, and segments 5-2, of which one end is supported within cover 4 so that it is free to swing. The opposite ends of segments 5-1 and 5-2 are connected to each other. When cover 4 is closed, hinges 5 are bent; when it is opened, they extend in a straight line.

With the finger-type blood pressure monitors pictured in FIGS. 1, 2 and 3, cuff 2 is folded and returned to chamber 3 when cover 4 is closed. In this closed state, nothing protrudes from main unit 1, which assumes the form of a compact rectangular box. For portability when the unit is not in use, the blood pressure monitor assumes a smaller (thinner) shape; it is less bulky and therefore more convenient. When cover 4 is opened, finger cuff 2 pops out of chamber 3 and assumes the form of a cylinder into which the user can insert a finger. There is thus no need to extract the cuff from its chamber independently of opening the cover, which simplifies the operation of the monitor.

Figure 4:
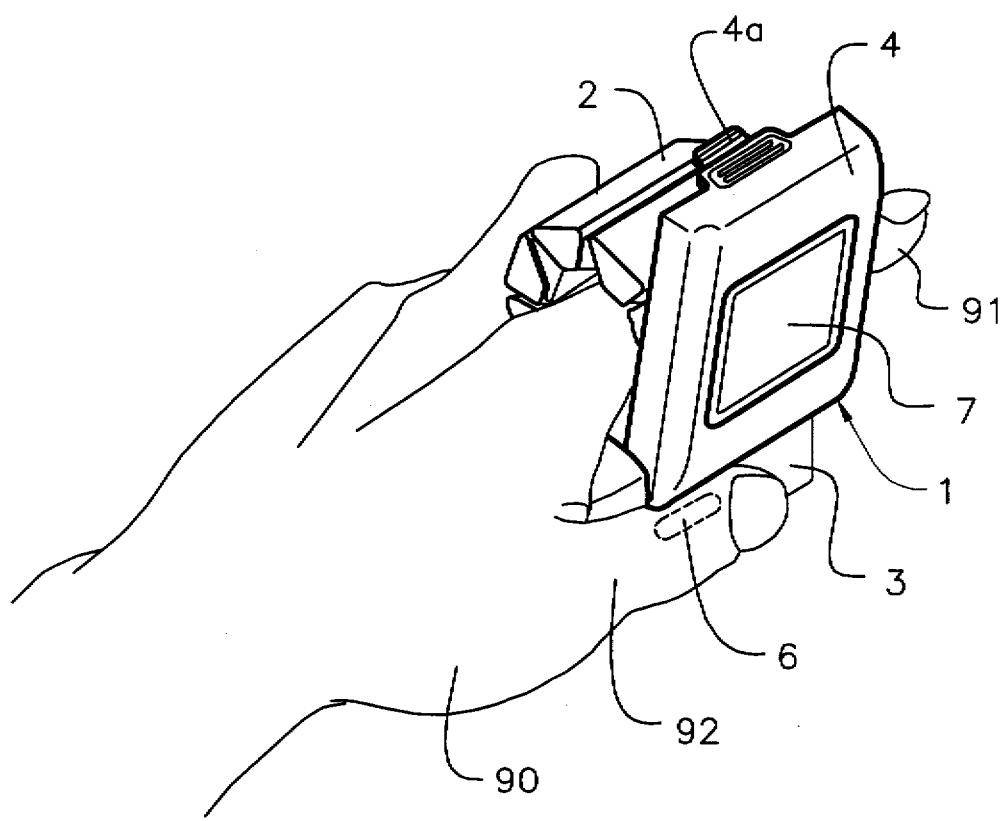
FIG. 4 illustrates how a person uses the blood pressure monitor shown in FIGS. 1 and 2.

The blood pressure monitors pictured in FIGS. 1 and 2 are used as shown in FIG. 4. When cover 4 has been opened, the user inserts, for example, the index finger 91 of left hand 90 into cuff 2. Left thumb 92 is then in contact with the side of chamber 3. As he holds chamber 3 (or main unit 1) in the left hand, he can actuate start button 6 with the left thumb. If the user uses the right hand, the right index finger is inserted into cuff 2 from the opposite direction. The right thumb is then in contact with the side of chamber 3, and the user can actuate the start button with it. The user can thus make a one-handed measurement using either hand. Since display 7 is on the outside of cover 4, it can be seen easily during the measurement.

In FIG. 2 each hinge 5 has a protruding cam 8, and each side of chamber 3 has a stop 9. Cams 8 and stops 9 constitute the mechanism to limit the angle to which the cover can open. When cover 4 is closed, cams 8 and stops 9 are positioned as shown in FIG. 2 (a). When cover 4 is opened to a certain degree, cams 8 will engage with stops 9, and hinges 5 will be prevented from rotating further, thus fixing cover 4 in the open position. The angle at which cover 4 is arrested by cams 8 and stops 9 should be determined so that when the user inserts an index finger in cuff 2 and grasps main unit 1 or chamber 3 with the same hand, pulse sensors 10 are positioned in the vicinity of the pulse of the index finger. This will insure that the pulse can be measured accurately when the finger is in the measurement position.

Figure 5A:
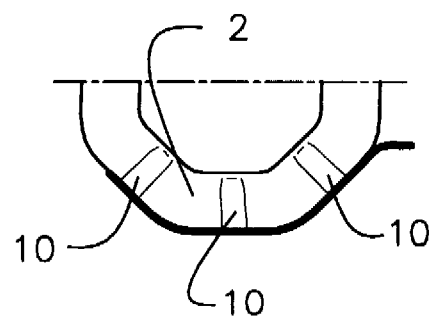
FIG. 5 (a) shows a partial lateral view of a flexible printed circuit board which might be attached to the finger cuff.
FIG. 5(b) shows a partial frontal view of the circuit board of FIG. 5(a).
Figure 5B:
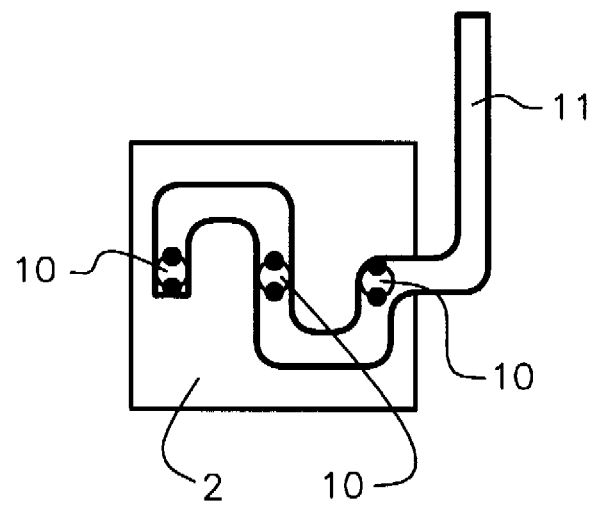

As is shown in FIG. 5, the three photoelectric pulse sensors 10 are electrically connected to S-shaped flexible printed circuit (FPC) board 11, which is fixed to the outer periphery of finger cuff 2. Making FPC 11 an S-shape rather than the more usual straight line has the result that the load on photoelectric sensors 10 does not vary when the shape of the periphery of cuff 2 changes for storage or measurement. This increases the service life of the monitor.

Figure 6A:
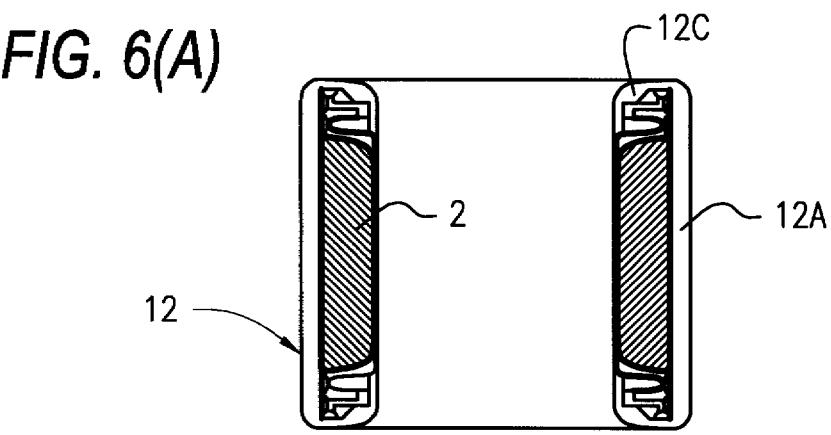
FIG. 6(a) is a cross section taken along line B—B in FIG. 6(b)
Figure 6B:
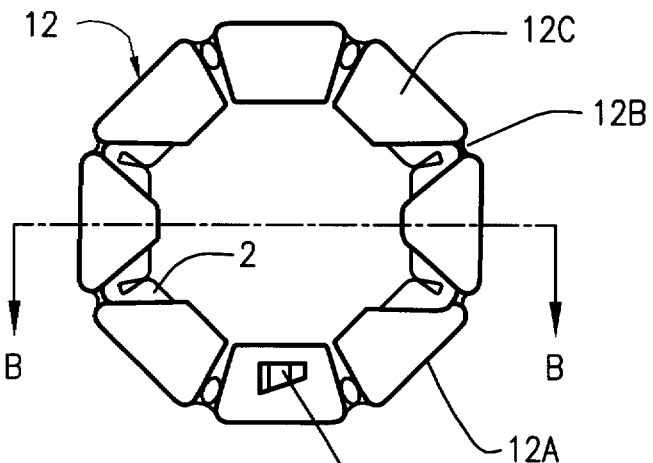
FIG. 6(b) is a frontal view.
Figure 6C:
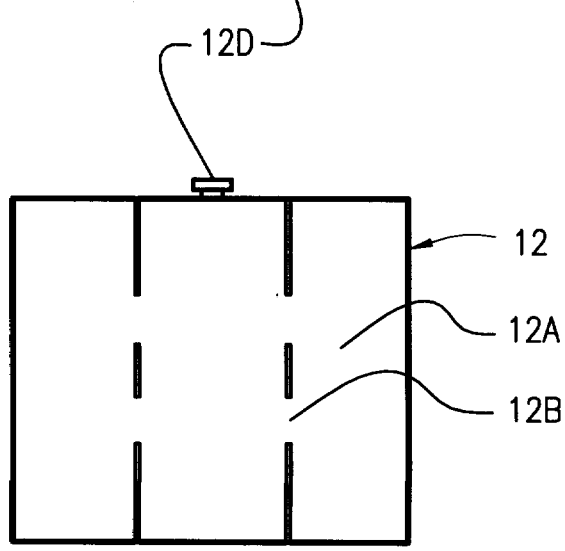
FIG. 6(c) is a lateral view.
Figure 7:
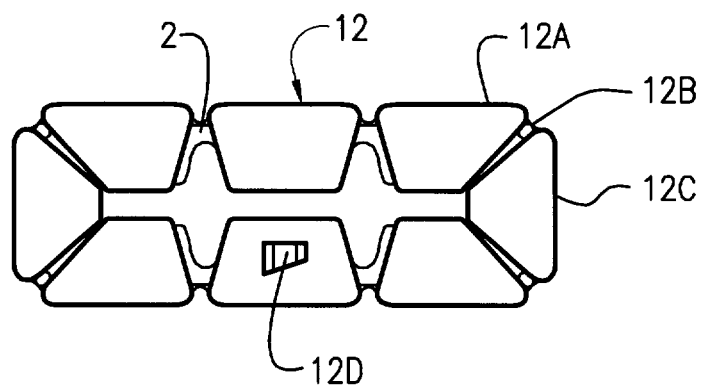
FIG. 7 is a frontal view of the finger cuff shown in FIG. 6 when folded up.

Finger cuff 2 may be a common type of flexible cuff, or it may have the design shown in FIGS. 6 and 7. The outer surface and both sides of cuff 2 in FIG. 6 are shrouded by collar 12. Collar 12 comprises a number of rectangular peripheral plates 12A which are connected by two hinges 12B. On either end of each peripheral plate 12A, a wall 12C extends at a right angle. Peripheral plates 12A enclose the outer periphery of finger cuff 2, and walls 12C enclose its sides. Using collar 12 to enclose cuff 2 allows the cuff to be contained efficiently in a chamber 3 with right angles. The purpose of placing walls 12C on either side of collar 12 is to prevent the cuff from expanding in the axial direction when it is inflated. Rather, it will expand efficiently in the centripetal direction as it is inflated with pressurized air.

Figure 8:
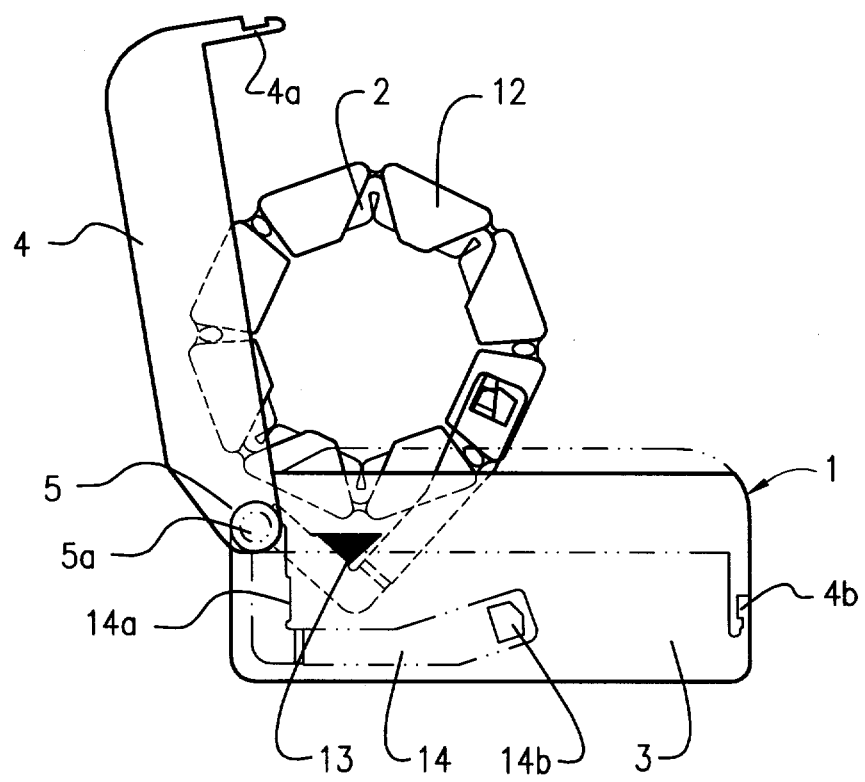
FIG. 8 is a lateral view of another embodiment of a finger-type blood pressure monitor employing the finger cuff of FIG. 6, shown when open.

A finger-type blood pressure monitor with a cuff 2 sheathed in a collar 12 like that described above is pictured in FIG. 8. In this type of monitor, a portion of collar 12 is fixed to the interior of cover 4, and arm 14 is fixed to a location facing the spot where collar 12 is attached. Arm 14 is fastened to shaft 5a on hinge 5 in such a way that it is free to swing. It has a protrusion 14a on its lower end and a slot 14b on its upper end which serves to engage the cuff. Tab 12D (see FIGS. 6 and 7) on wall 12C of collar 12 engages with slot 14b, and when collar 12 (i.e., finger cuff 2) moves, arm 14 moves concurrently. Stop 13, with which protrusion 14a on arm 14 comes in contact, is formed in an appropriate location on the interior surface of chamber 3. When protrusion 14a makes contact with stop 13, the movement of arm 14 is arrested. Cover 4 can continue to open until it reaches its maximum limit. When cover 4 is opened, then, it draws collar 12 together with finger cuff 2 in one direction while arm 14 draws them simultaneously in the opposite direction. Finger cuff 2 opens into a cylindrical shape into which the user can easily insert a finger without delay. The cylindrical form restoring device to restore the cuff to its cylindrical form thus includes primarily arm 14, tab 12D and stop 13.

Figure 9A:
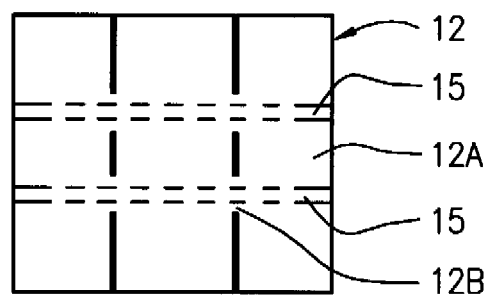
FIG. 9 (a) shows a lateral view and FIG. 9(b) a frontal view of the finger cuff of FIG. 6 equipped with spring plates.
Figure 9B:
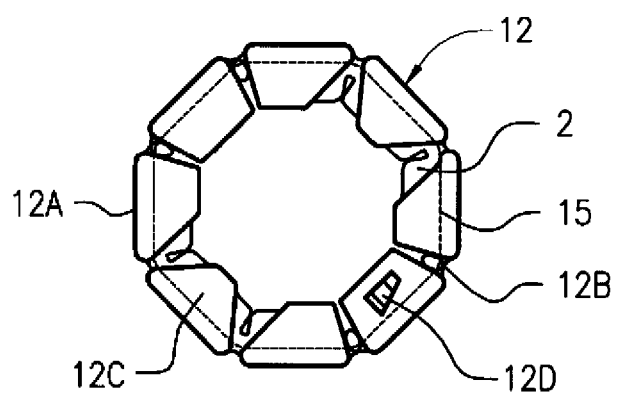

Another example of a cylindrical form restoring device to restore the cuff to its cylindrical form is shown in FIG. 9. Spring plates 15 are interposed between cuff 2 and collar 12 on the side nearer the outer periphery. The spring plates 15 shown here are annular plates which pass through hinges 12B in collar 12. Two of these plates run along the outer periphery of finger cuff 2. When spring plates 15 are used, the force required to restore cuff 2 to its cylindrical shape is constantly available. As soon as cover 4 is opened, cuff 2 will pop out and resume its cylindrical form.

Figure 10:
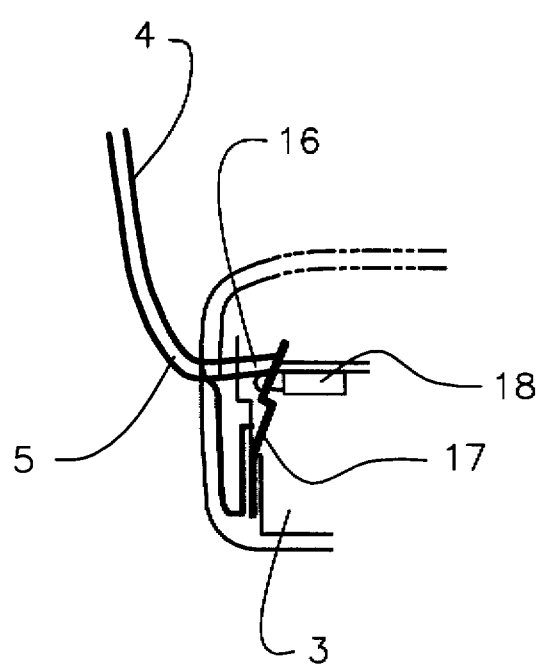
FIG. 10 is a partial cross section of an example of a device to detect when the cuff is open.

The mechanism pictured in FIG. 10 is an example of a cover detector to detect when cover 4 is open. This cover detector comprises cam 16, which is formed on the end of hinge 5 on cover 4; elastic plate 17, which extends in chamber 3 toward cam 16; and switch 18, which is turned on and off by elastic plate 17. When cover 4 is closed, cam 16 is not in contact with elastic plate 17, and switch 18 remains off. When cover 4 is opened, cam 16 presses on elastic plate 17. When cover 4 is completely open, switch 18 is switched on by plate 17, causing the fact that the cover is open to be detected.

When such a detector is used, the cover detector can be designed so that the power supply is connected when switch 18 goes on. This will obviate the need to switch the power supply on and further simplify the measurement operation. The cover detector may also be configured so that the cuff is pressurized automatically once a given time interval had elapsed after switch 18 went on. This will also obviate the need to initiate pressurization of the cuff, making the measurement operation even simpler. If the cuff is to be pressurized automatically, it should be pressurized a fixed interval after the aforesaid pulse detectors (photoelectric sensors) 10 have detected that a finger has been inserted in the cuff.

The cover detector can then be configured so that the cuff will not be pressurized if the operating button (i.e., the pressure switch) 6 is actuated while switch 18 is off. This will insure that the cuff will not be pressurized unintentionally or accidentally while cover 4 is closed (for example, while the monitor is being transported). If the cover detector is so configured that if switch 6 is depressed when cover 4 is closed, it switches the monitor to memory access mode, the same switch can serve as both the pressure and the memory access switch. This will reduce the number of operating switches and decrease the cost of the monitor. Memory access mode allows the user to read out from the memory a previous measurement value which is shown on display 7.

Figure 11A:
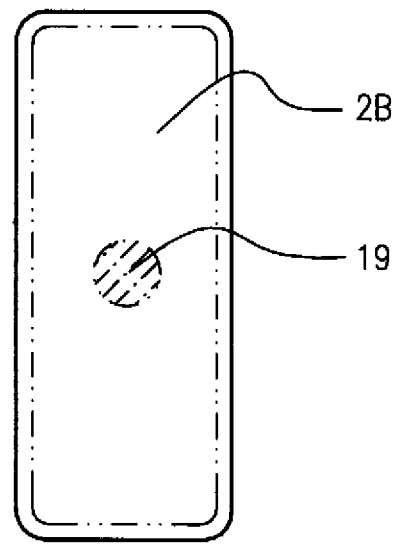
FIG. 11 (a) is a magnified plan view of a portion of a cuff of this invention containing a pulse sensor.
FIG. 11(b) is a magnified cross section of the same portion.
Figure 11B:
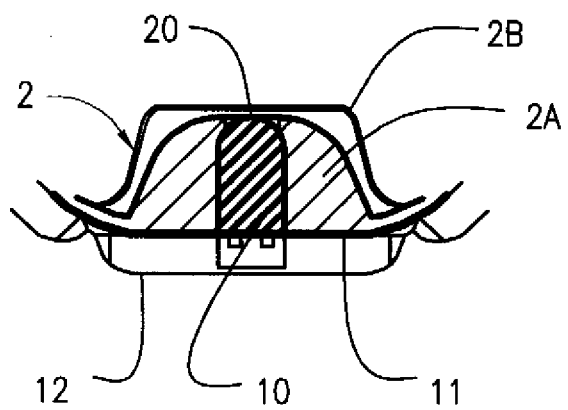

Photoelectric pulse sensors 10 detect the pulse in the user's finger. To optimize measurement accuracy, they should be configured as shown in FIG. 11. Finger cuff 2 includes an outer cuff 2A, which is inflated with pressurized air, and inner cuff 2B, which covers cuff 2A. The portions (sensor windows 19) of cuff 2B which face pulse sensors 10, which are mounted in outer cuff 2A, should have an infrared transmission factor which is higher than that of the surrounding portion of the cuff. For example, a semitransparent silicone rubber could be used for inner cuff 2B, and the inner and outer surfaces of sensor windows 19 could be made smooth. Such a design would insure that the elasticity of sensor windows 19 would not suffer and uniform elasticity would be maintained. The ability to pressurize cuff 2 would not be affected and measurement accuracy would remain high.

Another way to implement the windows would be to make outer cuff 2A black and reinforce its surface. Then outer cuff 2A would have low infrared transparency, and slits 20 could be provided in the portions of the cuff facing pulse sensors 10. This would make it difficult for stray light to strike the photodetectors in pulse sensors 10 and so would enhance their pulse detection function.

Figure 12:
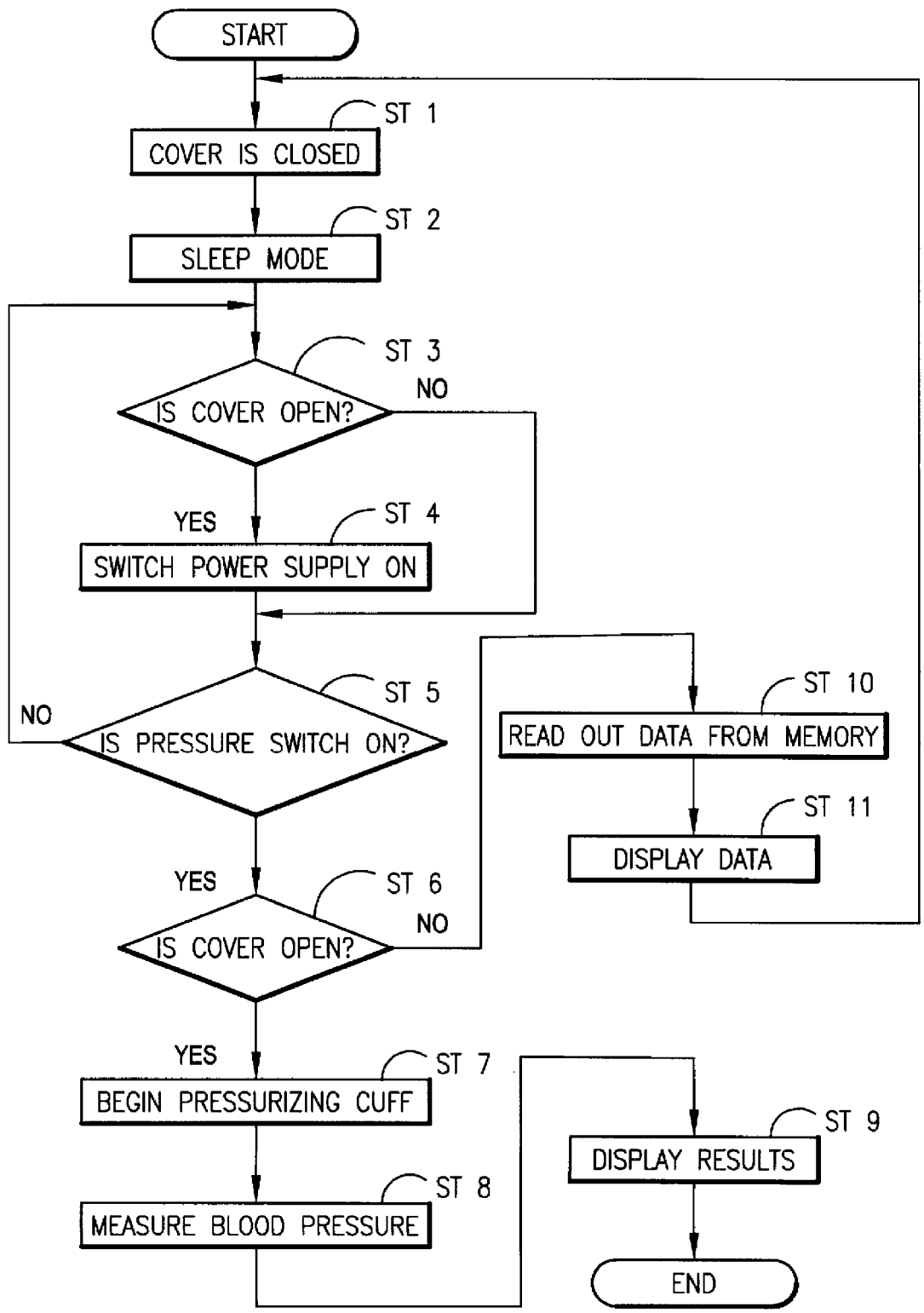
FIG. 12 is a flow chart of the entire operation of the blood pressure monitor of this invention.
Figure 13:
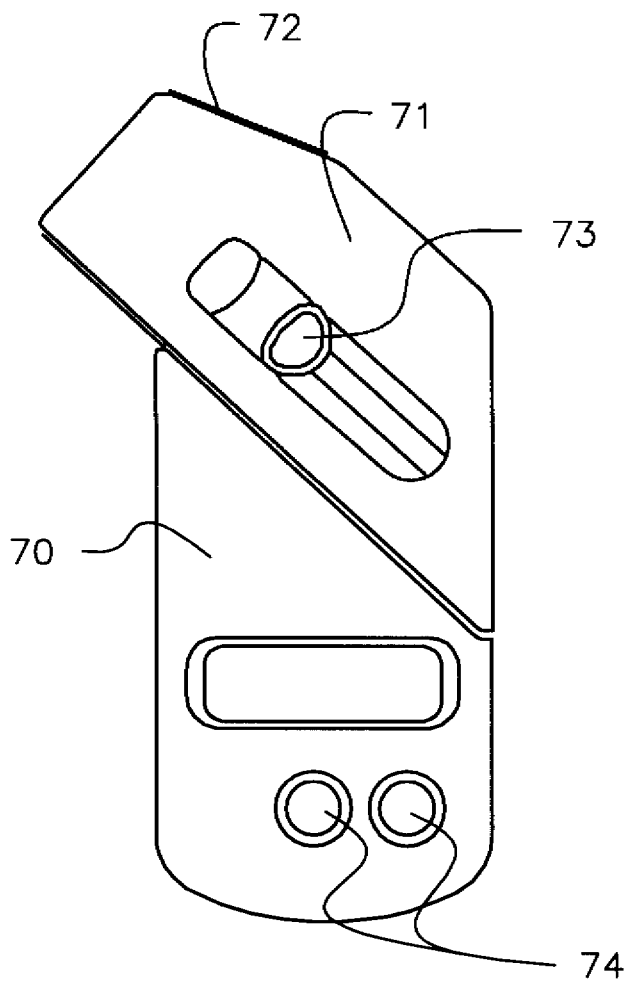
FIG. 13 shows a finger-type blood pressure monitor which is an example of the prior art.
Figure 14:
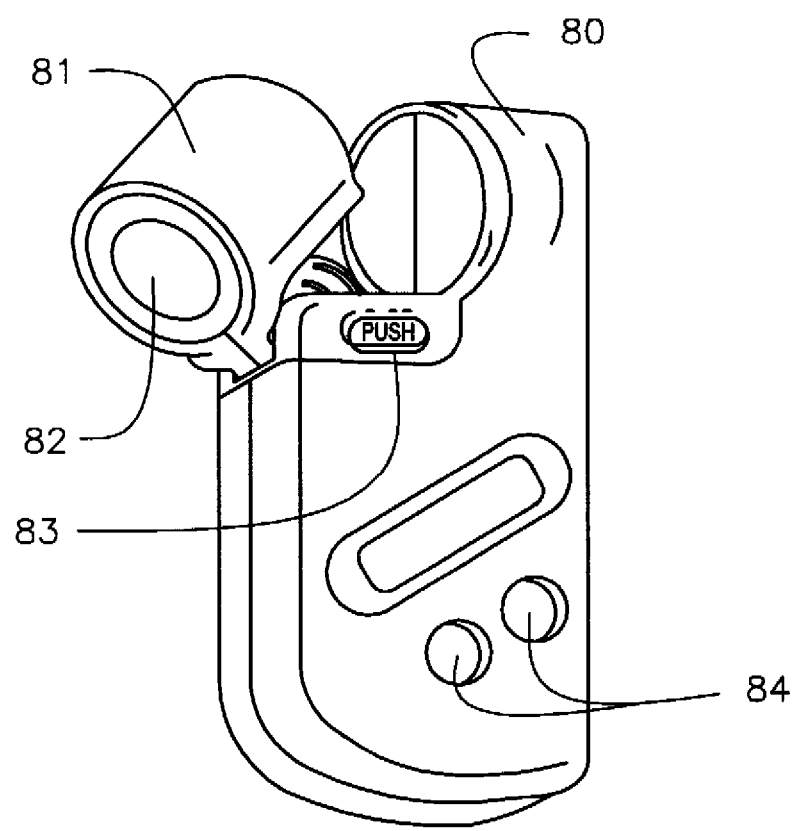
FIG. 14 shows another finger-type blood pressure monitor which is an example of the prior art.

We shall next discuss the overall operation of the finger-type blood pressure monitor described above, with reference to the flow chart in FIG. 12. When the monitor is not in use (when it is being transported or at other times) it remains in a sleep mode, during which time cover 4 is closed. In this state we pass through Steps 1 and 2 and proceed to Step 3. In Step 3 a judgment is rendered as to whether cover 4 is open or closed. If it is closed, we proceed to Step 5; if it is open, the power supply is switched on in Step 4 and we then proceed to Step 5. In Step 5 a judgment is rendered as to whether pressure switch 6 is on or off. If it is off, we return to Step 3, repeat Steps 3 through 5 and stand by. If switch 6 is on, in Step 6 we again render a judgment as to whether cover 4 is open. If the judgment is "no" and pressure switch 6 is depressed while cover 4 is closed, the cuff is not pressurized and the data are read out of the memory (Step 10). The value of the measurement made at some previous time is displayed on display 7 (Step 11), and we return to Step 1 and repeat the processing described above.

If the answer in Step 6 is "yes," then switch 6 is being depressed while cover 4 is open. We therefore begin the normal measurement operation. The cuff is pressurized (Step 7), the maximum and minimum blood pressure values are established (Step 8) and the results are displayed on display 7 (Step 9). As can be understood from this description, when the pressure switch is depressed while the cover is closed, the previous measurement value is displayed and the monitor waits in stand-by mode. Only when the switch is depressed while the cover is open will the cuff be pressurized and a measurement executed.

With one type of finger-type blood pressure monitor of this application, the cuff is returned to the chamber in the main unit when the cover of the monitor is closed so that it can be stored compactly. Closing the cover thus has the effect of reducing the size of the monitor so that it is not bulky to transport.

With another type of finger-type blood pressure monitor of this application, the cuff reverts to its cylindrical form as soon as the cover is opened, so it is immediately ready for a finger to be inserted in it. This obviates the need to pull out the cuff after opening the cover, thus simplifying the operation of the monitor.

The finger-type blood pressure monitor of this application may have an operating button on the portion of the cover or main unit which the user can reach with the thumb when the index finger is in the cuff. This allows the user to actuate the button with the thumb of the same hand that the measurement is being made on. It is thus possible to operate this blood pressure monitor using only one hand.

With the finger-type blood pressure monitor of this application, it is possible that the cuff is not pressurized when the actuating switch is depressed unless the detector for that purpose has detected that the cover is open. Thus the cuff will not be pressurized when the actuating switch is tripped accidentally while the monitor is in transit, and accidental operation is effectively prevented.

With the finger-type blood pressure monitor of this application, the pressure switch can function as the memory access switch unless the detector has detected that the cover is open. In other words, the same switch can be used to pressurize the cuff and to access the memory. This has the effect of reducing the number of operating switches so that the monitor can be produced at a lower cost.

The pulse sensors may be photoelectric sensors which are mounted on an S-shaped flexible circuit board attached to the cuff. This makes the cuff highly resistant to deformation.

The infrared transmission factors of the portions of the cuff which face the pulse sensors may be made higher than that of the surrounding portion of the cuff. This insures that the elasticity of the cuff and its ability to undergo pressurization will not be diminished and so enhances the accuracy of the measurement.

What is claimed is:

1. A finger-type cuff assembly for use with a blood pressure monitor, comprising:
    a main unit;
    a cover attached to said main unit in a way such that said cover can open and close;
    a foldable finger cuff of which a portion is fixed to an inside of said cover, said foldable finger cuff configured to open when said cover is opened; and
    a chamber disposed between said main unit and said cover to contain said foldable finger cuff when said cover is closed.

2. A finger-type blood pressure monitor according to claim 1, wherein said foldable finger cuff is configured to assume a cylindrical shape when said cover is opened for measuring blood pressure, and is configured to be accommodated in said chamber when said cover is closed and is not in use.

3. A finger-type blood pressure monitor according to claim 2, wherein said cover has a hinge to open and close with respect to said main unit.

4. A finger-type blood pressure monitor according to claim 3, wherein said hinge is located on a side of said main unit closest to a thumb of a user when an index finger of the user is inserted into said foldable finger cuff.

5. A finger-type blood pressure monitor according to claim 4, further comprising an operating button on said main unit or said cover.

6. A finger-type blood pressure monitor according to claim 4, further comprising a display on said cover.

7. A finger-type blood pressure monitor according to claim 3, further comprising a device to fix the maximum angle to which said cover can open so that a sensor mounted in said foldable finger cuff to detect a pulse of said index finger will be positioned in a vicinity of an artery of said index finger.

8. A finger-type blood pressure monitor according to claim 2, wherein an outer periphery of said foldable finger cuff is shielded by a plurality of collars comprising a plurality of peripheral plates connected by hinges.

9. A finger-type blood pressure monitor according to claim 8, wherein said foldable finger cuff comprises a wall on either end of said peripheral plates which shields a lateral portion of said cuff.

10. A finger-type blood pressure monitor according to claim 2, further comprising a cylindrical form restoring device for restoring said foldable finger cuff to a cylindrical form when said cover is opened.

11. A finger-type blood pressure monitor according to claim 10, wherein said cylindrical form restoring device is configured to draw said foldable finger cuff toward opposite side of a fixed portion of said cover.

12. A finger-type blood pressure monitor according to claim 10, wherein said cylindrical form restoring device comprises a spring plate interposed between said cuff and a collar which is forced to open said cuff.

13. A finger-type blood pressure monitor according to claim 1, wherein said foldable finger cuff is oriented so that a user can insert a finger into said cuff when said cuff is open.

14. A finger-type blood pressure monitor according to claim 1, further comprising a cover detector to detect said cover is open.

15. A finger-type blood pressure monitor according to claim 14, wherein said cover detector comprises a cam and a switch which is operated by said cam.

16. A finger-type blood pressure monitor according to claim 14, wherein said cover detector switches on a power supply when said cover detector detects said cover is open.

17. A finger-type blood pressure monitor according to claim 14, wherein said cover detector begins a pressurization of said foldable finger cuff only when said cover detector detects said cover is open.

18. A finger-type blood pressure monitor according to claim 14, further comprising a pressure switch to begin a pressurization of said foldable finger cuff, wherein said pressure switch will not function unless said cover detector detects said cover is open.

19. A finger-type blood pressure monitor according to claim 14, further comprising a pressure switch to begin a pressurization of said foldable finger cuff, wherein said pressure switch will function as a memory access switch when said cover detector detects said cover is closed.

20. A finger-type blood pressure monitor according to claim 1, wherein said main unit is divided into two sections of virtually the same size, in one of said two sections is provided said cover, said chamber for said finger cuff, and a display, and in another of said two sections is provided a mechanism to pressurize said finger cuff.

21. A finger-type cuff assembly for use in measuring blood pressure comprising:

a main unit;

a cover attached to said main unit in a way such that said cover can open and close;

a foldable finger cuff of which a portion is fixed to an inside of said cover, said foldable finder cuff being configured to open when said cover is opened; and a pulse sensor in said finger cuff including means for automatically pressurizing said finger cuff when said pulse sensor detects that a finger has been inserted in said finger cuff 22. A finger-type blood pressure monitor, comprising:

a main unit;

a finger cuff; and a pulse sensor in said finger cuff, wherein said pulse sensor comprises a photoelectric sensor mounted on an S-shaped flexible printed circuit board which is attached to said finger cuff.

23. A finger-type blood pressure monitor, comprising:

a main unit;

a cover attached to said main unit in a way such that said cover can open and close;

a foldable finger cuff of which a portion is fixed to an inside of said cover, said foldable finger cuff being configured to open when said cover is opened;; and a pulse sensor in said foldable finger cuff, wherein said pulse sensor is a photoelectric sensor, and an infrared transmission factor of a portion of said foldable finger cuff facing said pulse sensor is higher than that of an other portion of said foldable finger cuff.

24. A finger-type blood pressure monitor according to claim 23, wherein said finger cuff is made of material having low infrared transparency and said finger cuff has slits in a portion facing said pulse sensor.

* * * * *

UNITED STATES PATENT AND TRADEMARK OFFICE
CERTIFICATE OF CORRECTION

PATENT NO. : 5,807,266
DATED : September 15, 1998
INVENTOR(S) : Itonaga, et al

It is certified that error appears in the above-identified patent and that said Letters Patent is hereby corrected as shown below:

On the title page, insert the following:
-- item [30] Foregin Application Priority Data May 25, 1995 [JP] Japan.................................7-126113 ---

Signed and Sealed this

Twenty-third Day of February, 1999

Attest:

Q. TODD DICKINSON

*Attesting Officer*      *Acting Commissioner of Patents and Trademarks*